US00PP14767P2

(12) United States Plant Patent
Unger

(10) Patent No.: US PP14,767 P2
(45) Date of Patent: May 11, 2004

(54) THUNBERGIA PLANT NAMED 'ORANGE WONDER'

(50) Latin Name: *Thunbergia alata*
Varietal Denomination: Orange Wonder

(75) Inventor: Michael H. Unger, Rheinfelden (DE)

(73) Assignee: Unger Breeding, Rheinfelden (DE)

( * ) Notice: Subject to any disclaimer, the term of this patent is extended or adjusted under 35 U.S.C. 154(b) by 0 days.

(21) Appl. No.: 10/113,593

(22) Filed: Apr. 1, 2002

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Susan B. McCormick
(74) *Attorney, Agent, or Firm*—Wood, Phillips, Katz, Clark & Mortimer

(57) ABSTRACT

A new and distinct Thunbergia plant named 'Orange Wonder', characterized by its bright orange flowers, dark green leaves, good basal branching character and climbing, spreading growth habit.

1 Drawing Sheet

Latin name of the genus and species of plant claimed: *Thunbergia alata.*
Variety denomination: 'Orange Wonder'.

BACKGROUND OF THE INVENTION

The present invention comprises a new and distinct Thunbergia plant, botanically known as *Thunbergia alata*, and hereinafter referred to by the cultivar name 'Orange Wonder'.

The new Thunbergia resulted from the induced mutation of the seed variety *Thunbergia alata* (not patented). The 'Orange Wonder' cultivar was discovered and selected by the inventor in 1999, at Rheinfelden, Germany. 'Orange Wonder' is vegetatively reproduced rather than produced from seed, is more vigorous and has darker flower color than the parent.

Asexual reproduction of the new cultivar by terminal tip cuttings has demonstrated that the characteristics of the new cultivar as herein described are firmly fixed and retained through successive generations of such asexual propagation.

SUMMARY OF THE INVENTION

It was found that the cultivar of the present invention:

(a) exhibits bright orange flowers;

(b) forms dark green foliage;

(c) exhibits a good branching character; and (d) exhibits a vigorous climbing and trailing growth habit.

The new cultivar of the present invention can be compared to 'Susie Orange' (not patented). In side-by-side comparisons, plants of the new cultivar exhibit a more vigorous growth habit, and darker orange flowers than those of 'Susie Orange'.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for 14 weeks in a greenhouse at West Chicago, Ill.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Aug. 15, 2001. The readings were taken between 1:00 and 3:00 p.m. under natural daylight conditions. The plants were produced from cuttings taken from stock plants and were grown in a double poly carbonate covered greenhouse under conditions comparable to those used in commercial practice while utilizing a soilless growth medium. Temperatures of approximately 70° to 80° F. (21° to 26° C.) during the day and approximately 60° to 65° F. (15° to 18° C.) during the night and light levels between 5,000 and 8,000 were maintained. Plants used for the following descriptions and measurements were grown for 14 weeks from rooted cuttings.

Classification:
*Botanical.*—*Thunbergia alata* cultivar 'Orange Wonder'.

Propagation:
*Type cutting.*—Terminal tip.
*Time to initiate roots.*—*Approximately* 7–10 days.
*Time to develop roots.*—Approximately 14 to 21 days.
*Root description.*—Fibrous, branching.

Plant description:
*Form.*—Climbing and trailing.
*Habit of growth.*—Vigorous. Pinching improves basal branching. A mature plant, 14 weeks after the planting of a rooted cutting, commonly has an average of 3.6 branches.
*Branches.*—Wiry. Up to 145.7 cm long and 1 mm in diameter, with approximately 19 leaves per branch. Texture: Moderately to densely pubescent. Color: 144B when young and 200B when mature. Length of longest internode: Approximately 14.9 cm.
*Foliage.*—Leaves are non-fragrant, simple, opposite, at an acute angle to the stem, triangular to ovate, with dentate margin, acute apex and sagittate base. Upper and lower surfaces are densely pubescent. Leaf length is approximately 4.9 cm and width is approximately 3.9 cm. Upper surface is slightly darker than 143A, lower surface is closest to but more yellow than 137D. Both upper and lower surfaces have 5 nerved, palmate venation closest to 183D. Petiole length is approximately 2.9 cm, diameter, including wings, is approximately 5 mm. Texture: Very sparsely pubescent. Color: Closest to 137D with overlay of 183A. Wing color: Darker than 143A.

Flowering description:

*Flowering habit.*—Freely flowering.

*Natural flowering season.*—Year round in greenhouse environment; spring through autumn in outdoor garden.

*Flower type.*—Solitary, axillary, slaverform. Flowers are persistent.

*Peduncle.*—Strong, densely pubescent with acute angle, approximately 4.7 cm in length, less than 1 mm in diameter and 144A.

*Bud.*—Ovate, approximately 2.1 cm in length, 6 mm in diameter. Bud, just before opening, is 16C.

*Flower description.*—Non-Fragrant. Composed of five (5) petals fused at base to form a corolla tube. Corolla is round and aspect is flat. Diameter is approximately 4.4 cm. Petals are non imbricate, have sunken apices and entire margin. Petal size: Approximately 1.6 cm long from throat and 1.9 cm wide. Color of upper surface when fully opened is closest to but darker and brighter than 25A. Color of lower surface when fully opened is 25B. Corolla tube diameter: At throat it is approximately 1.2 cm in diameter and at base it is 3 mm in diameter. Corolla tube length: Approximately 2.5 cm. Throat texture: Upper ¼ is pubescent, rest is smooth. Throat color: 187A. Color of outer surface of corolla tube is 26B near opening and 79A at base.

*Sepals.*—Number: 5. Length: approximately 2.7 cm. Width: At base approximately 1.5 cm tapering to an acuminate tip. Texture: Outer surface is densely pubescent, inner surface is glabrous. Color: Outer surface is 138A, inner surface is 138B.

*Calyx.*—Approximately 4 mm in length. The outer surface is densely pubescent and 143A.

*Bracts.*—Number: Approximately 10. Length: Approximately 2.2 cm. Width: Approximately 1.6 cm. Color: 144B.

*Reproductive organs.*—Androecium: There are 4 stamens. Anther size: Less than 1 mm in length. Anther color: 11D. Pollen was not observed. Gynoecium: One pistil, 1.3 cm in length. Stigma length: 3 mm. Stigma color: 3D. Stigma texture: Smooth. Style length: 1.4 cm. Style color: 3D. Ovary diameter: 3 mm. Ovary color: 144B. Seed production: Seed production has not been observed.

Disease resistance: Resistance to diseases common to Thunbergia has not been observed.

I claim:

1. A new and distinct Thunbergia plant as herein described and illustrated.

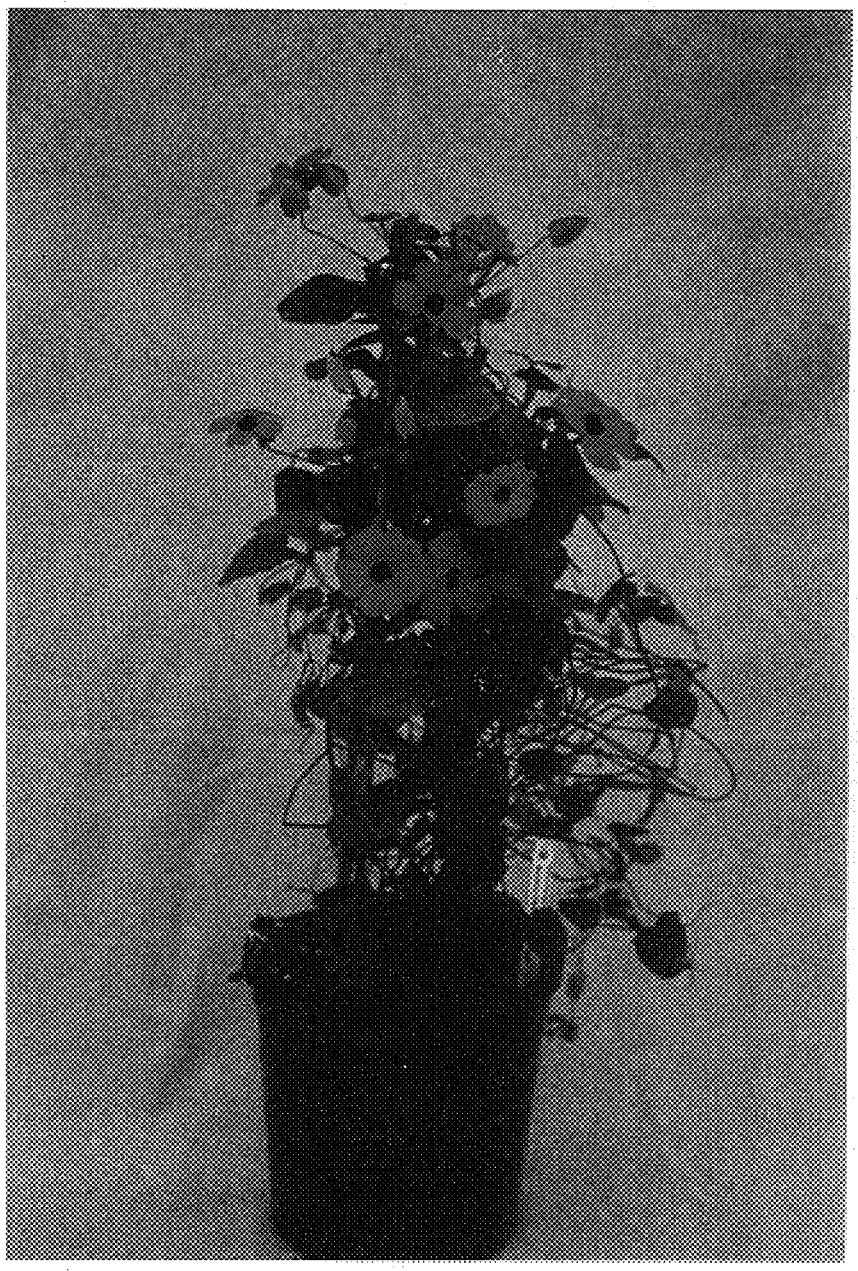

* * * * *